US007626058B2

United States Patent
van Cauwenberge et al.

(10) Patent No.: US 7,626,058 B2
(45) Date of Patent: Dec. 1, 2009

(54) PROCESSES FOR PRODUCING ETHYLENE AMINES

(75) Inventors: Gunther van Cauwenberge, Temse (BE); Johann-Peter Melder, Boehl-Iggelheim (DE); Kirsten Dahmen, Mannheim (DE); Klemens Massonne, Bad Duerkheim (DE); Steffen Oehlenschlaeger, Ludwigshafen (DE); Kai Michael Exner, Mumbai Powai (IN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/089,775

(22) PCT Filed: Oct. 6, 2006

(86) PCT No.: PCT/EP2006/067118

§ 371 (c)(1),
(2), (4) Date: Apr. 10, 2008

(87) PCT Pub. No.: WO2007/042466

PCT Pub. Date: Apr. 19, 2007

(65) Prior Publication Data

US 2008/0249307 A1  Oct. 9, 2008

(30) Foreign Application Priority Data

Oct. 11, 2005 (DE) .................. 10 2005 048 552

(51) Int. Cl.
*C07C 209/08* (2006.01)

(52) U.S. Cl. .................................................. 564/482
(58) Field of Classification Search ................. 564/482
See application file for complete search history.

(56) References Cited

U.S. PATENT DOCUMENTS

| 3,484,488 | A |   | 12/1969 | Lichtenwalter et al. |
|-----------|---|---|---------|----------------------|
| 3,882,181 | A | * | 5/1975  | Forster et al. ............... 564/482 |
| 4,014,933 | A |   | 3/1977  | Boettger et al.      |
| 4,568,746 | A |   | 2/1986  | Cowherd, III         |
| 2004/0073035 | A1 | | 4/2004  | Maase et al.         |
| 2005/0020857 | A1 | | 1/2005  | Volland et al.       |

FOREIGN PATENT DOCUMENTS

| GB | 1508460       | 4/1978 |
| WO | WO 03/062171  | 7/2003 |

OTHER PUBLICATIONS

Arné, M., "Alkylamines", SRI International, 1981, PEP Report No. 138.

* cited by examiner

*Primary Examiner*—Brian J Davis
(74) *Attorney, Agent, or Firm*—Connolly Bove Lodge & Hutz LLP

(57) ABSTRACT

Processes are described comprising: (i) providing a reactant comprising 1,2-dichloroethane; and (ii) reacting the reactant with ammonia to form a reaction product comprising one or more ethylene amines and hydrogen chloride, wherein the reaction is carried out in the presence of an organic, nitrogen- or phosphorus-containing compound which reacts with the hydrogen chloride to form an ionic liquid.

19 Claims, 4 Drawing Sheets

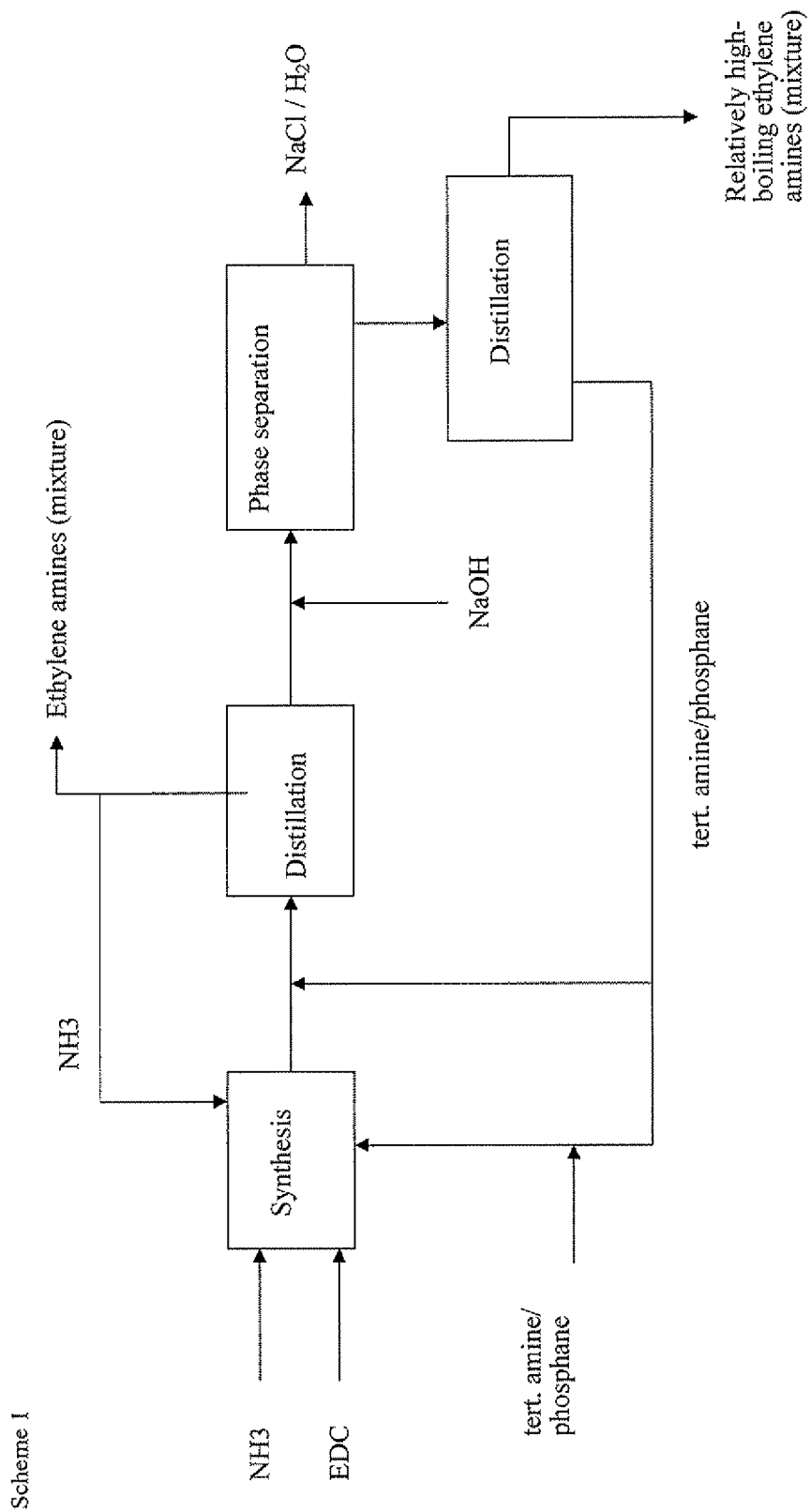
Scheme 1

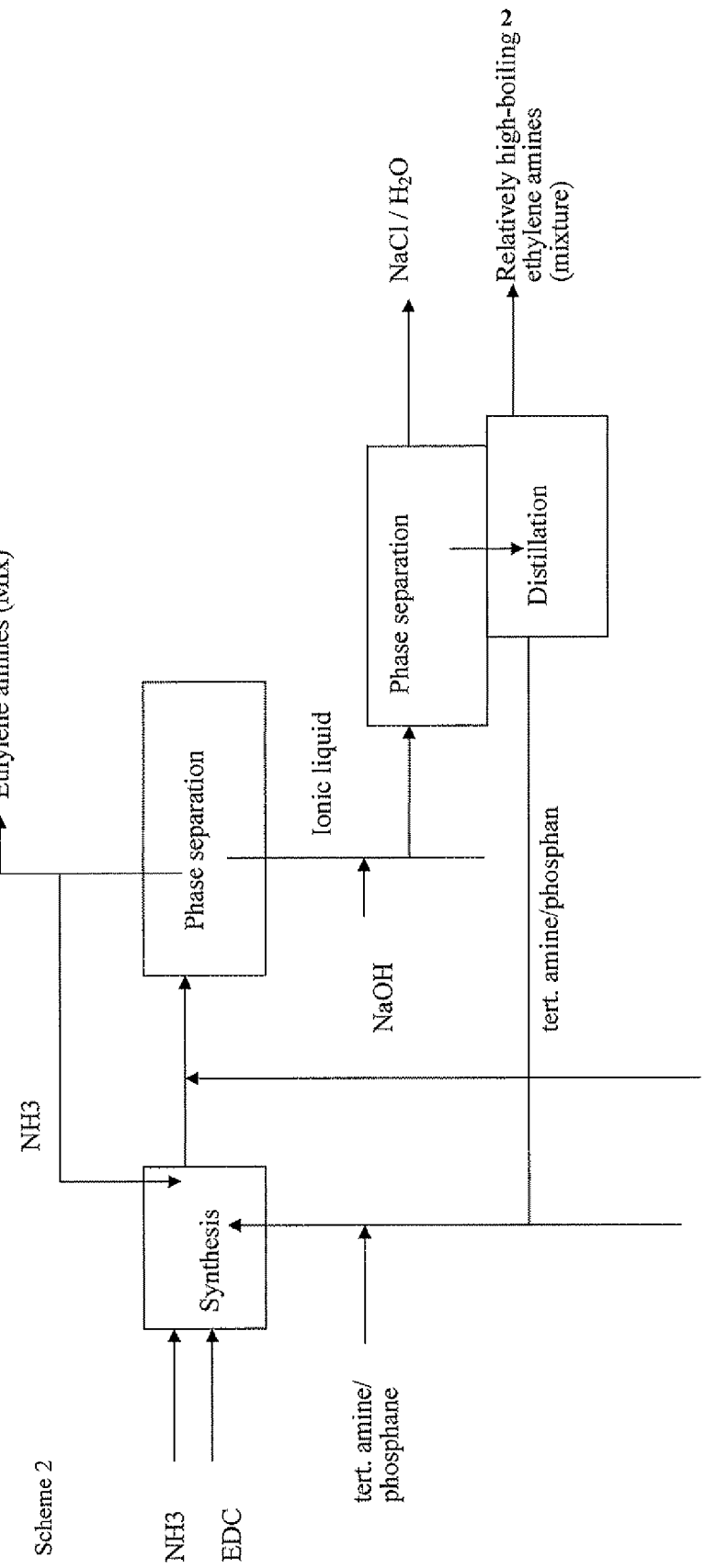

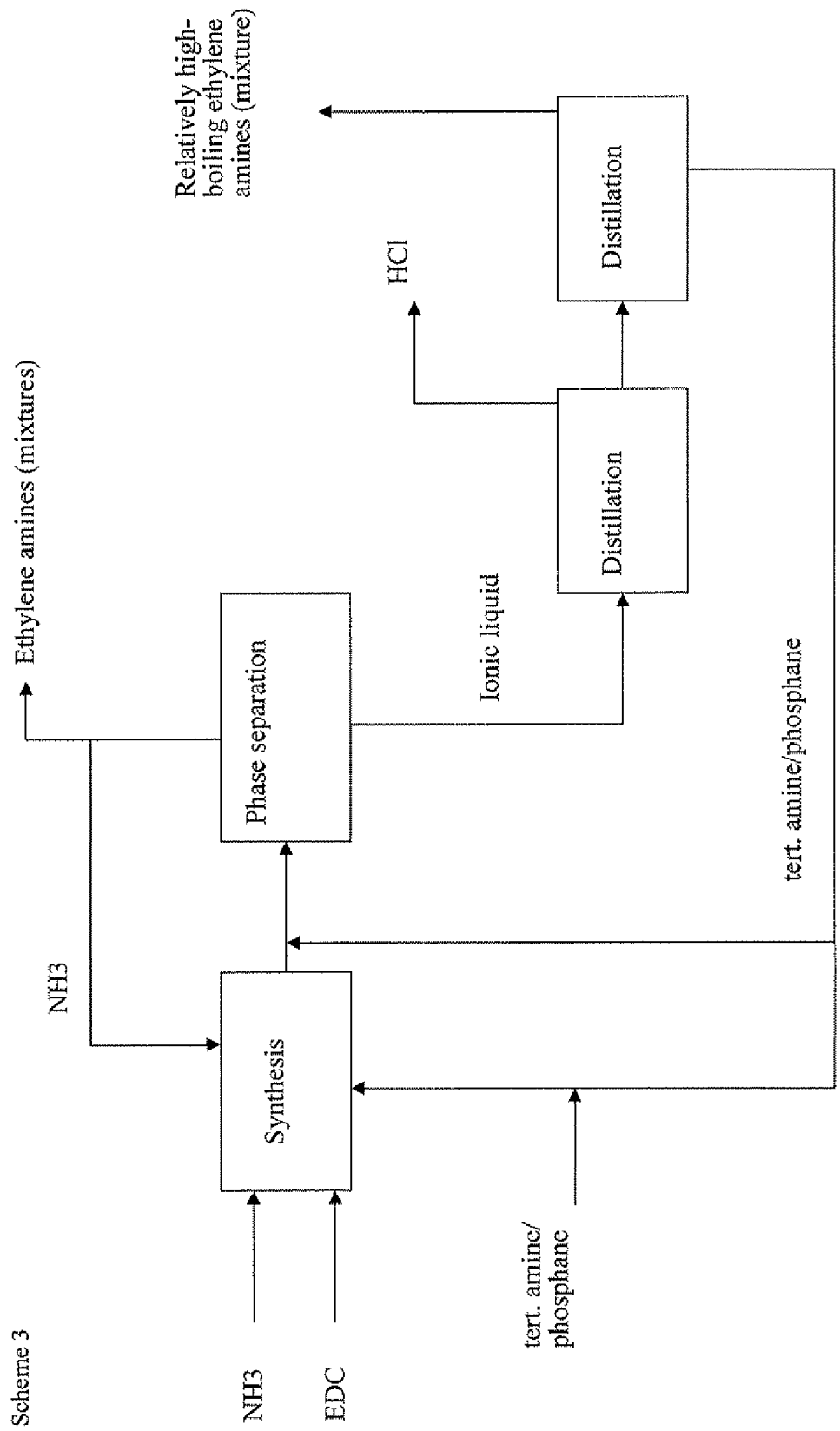

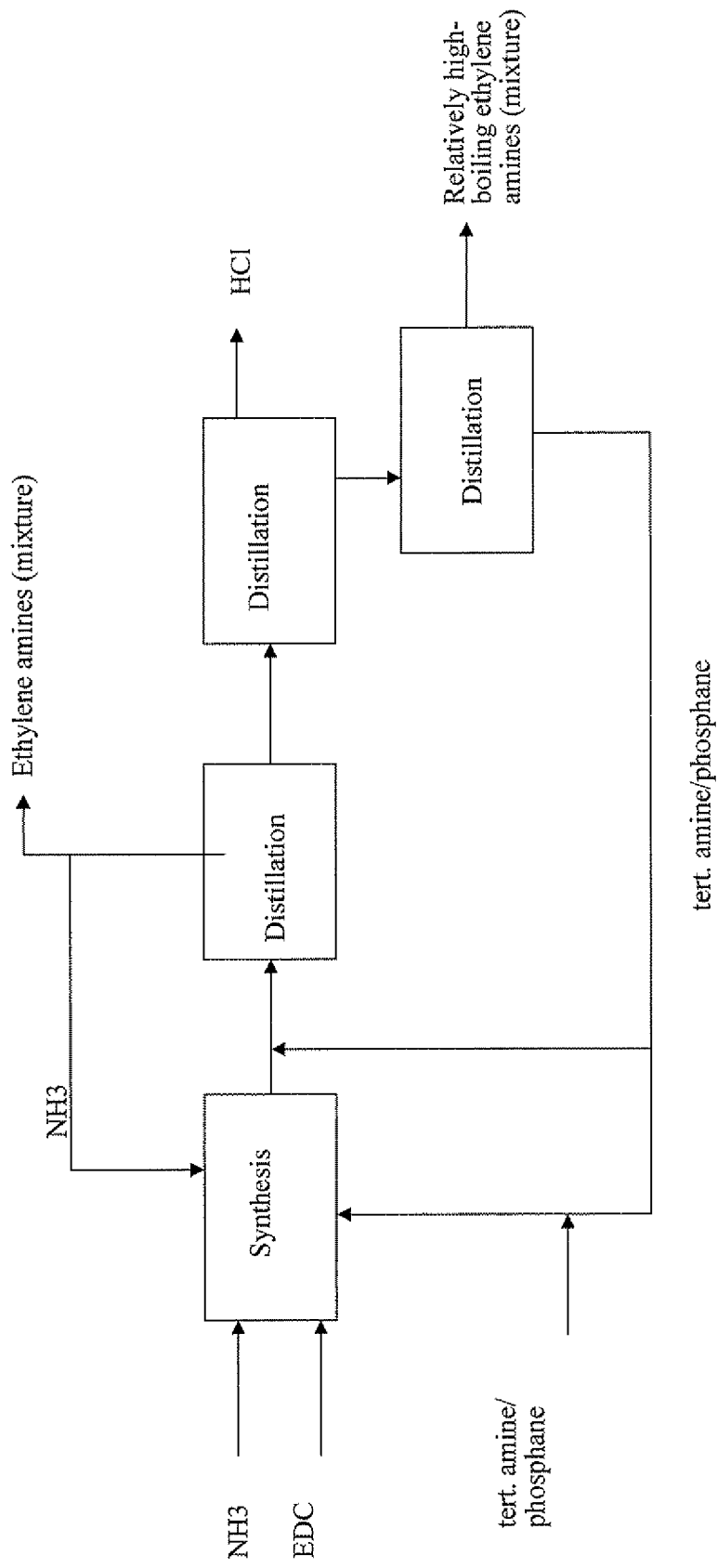

PROCESSES FOR PRODUCING ETHYLENE AMINES

CROSS-REFERENCE TO RELATED APPLICATIONS

This application is a national stage application, under 35 U.S.C. §371, of PCT/EP2006/067118, filed Oct. 6, 2006, which claims priority of German Patent Application No. 102005048552.9, filed Oct. 11, 2005.

BACKGROUND OF THE INVENTION

Ethylene amines are used, inter alia, as solvents, stabilizers, for the synthesis of chelating agents synthetic resins, drugs, inhibitors and surface-active substances.

Ethylendiamine (EDA) and diethylenetriamine (bis(2-aminoethyl)amine; DETA) are used, in particular, as solvents for dyes and are starting materials for producing ion exchangers, pesticides, antioxidants, corrosion inhibitors, complexing agents, textile assistants and absorbents for (acidic) gases.

Numerous methods of preparing ethylene amines, in particular EDA and DETA, have been described in the literature.

Ethylene amines are produced, in particular, by means of two different technologies.

The amination of monoethanolamines by means of ammonia over transition metal catalysts gives a mixture of ethylenediamine (EDA), diethylenetetramine (DETA), aminoethylethanolamine (AEEA) and piperazine (PIP) and also small proportions of higher ethylene amines.

Amination of monoethanolamine (MEOA) by means of ammonia (cf., for example, PEP Report No. 138, "Alkyl Amines", SRI International, Mar. 3, 1981 and U.S. Pat. No. 4,014,933 (BASF AG)) enables the formation of these higher ethylene amines (i.e. ethylene amines having a boiling point above that of triethylenetetramine (TETA)) to be largely suppressed in favor of ethylenediamine. However, aminoethylethanolamine (AEEA) and piperazine (PIP) are formed as by-products in this reaction.

The conversion of EDA into DETA over transition metal catalysts is known, for example, from GB-A-1,508,460 (BASF AG) and U.S. Pat. No. 4,568,746 (UCC)).

A second technology starts out from 1,2-dichloroethane (EDC) which is reacted with ammonia to form ethylene amines, with the hydrochlorides of the abovementioned ethylene amines being obtained first.

According to PEP Report No. 138, "Alkyl Amines", SRI International, Mar. 3, 1981, in particular pages 7, 8, 13-16, 43-107, 113, 117, the reaction of dichloroethane with ammonia at molar ratios of 1:15 gives diethylenetriamine (DETA) with a proportion of ethylene amines formed of greater than 20% by weight. However, in addition to 40% by weight of ethylenediamine (EDA), 40% by weight of higher ethylene amines are obtained.

Furthermore, the hydrochlorides of the higher ethylene amines triethylenetetramine (TETA), tetraethylenepentamine (TEPA) and pentaethylenehexamine (PEHA) are additionally formed. The reaction with ammonia to form the hydrochlorides is carried out in aqueous solution. The hydrochlorides are therefore obtained in solution and the amines are set free therefrom by addition of equimolar amounts of sodium hydroxide, i.e. an aqueous solution of the ethylene amines EDA (30-50% by weight), DETA (20-30% by weight), higher ethylene amines (30-40% by weight) and large amounts of sodium chloride is obtained as the crude product mixture. In the work-up of this mixture, all of the water is generally distilled off first. In a second step, all of the sodium chloride is then separated as a solid from the amines.

Disadvantages here are, in particular, the energy-intensive distillation of water and the removal of the sodium chloride (NaCl) as a solid.

BRIEF SUMMARY OF THE INVENTION

The present invention relates to a process for preparing ethylene amines by reacting 1,2-dichloroethane (EDC) with ammonia.

It was an object of the present invention to remedy one or more disadvantages of the prior art and to discover an improved economical process for preparing ethylene amines, in particular ethylenediamine (EDA), diethylenetriamine (DETA), piperazine (PIP), triethylenetetramine (TETA) and/or higher linear polyethylene amines (e.g. tetraethylenepentamine (TEPA), pentaethylenehexamine (PEHA)).

We have accordingly found a process for preparing ethylene amines by reacting 1,2-dichloroethane (EDC) with ammonia, in which the reaction is carried out in the presence of an organic nitrogen or phosphorus compound which reacts with hydrogen chloride (HCl) to form an ionic liquid (IL).

The process products prepared according to the invention are, in particular, EDA and/or DETA.

The reaction proceeds, for example, firstly according to the following equations:

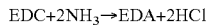

$$EDC + 2NH_3 \rightarrow EDA + 2HCl$$

$$EDA + EDC + NH_3 \rightarrow DETA + 2HCl$$

The ammonia is preferably used in liquid form or as an aqueous solution.

The HCl liberated in the reaction reacts, according to the invention, with the organic nitrogen or phosphorus compound to form a sufficiently thermally stable ionic liquid (IL) which also functions as solvent.

BRIEF DESCRIPTION OF THE DRAWINGS

FIG. 1 is a block diagram representation of an embodiment of a process according to the present invention;

FIG. 2 is a block diagram representation of another embodiment of a process according to the present invention;

FIG. 3 is a block diagram representation of another embodiment of a process according to the present invention; and FIG. 4 is a block diagram representation of another embodiment of a process according to the present invention.

DETAILED DESCRIPTION OF THE INVENTION

The organic nitrogen compound is preferably a tertiary amine or an N-heterocycle and the organic phosphorus compound is preferably a tertiary phosphane.

The tertiary amine preferably has a boiling point at atmospheric pressure (1 atm.=1.01325 bar) of greater than 100° C., particularly preferably greater than 200° C., in particular in the range from 250 to 400° C., and the corresponding acid obtained by protonation of the tertiary amine (an ammonium ion) preferably has a $pK_a$ at 25° C. of greater than 8.5, particularly preferably greater than 9.0, in particular in the range from 9.5 to 12.0.

The tertiary amine is particularly preferably a $C_{18-42}$-alkylamine, in particular a $C_{20-38}$-alkylamine, very particularly preferably a $C_{22-34}$-alkylamine.

Furthermore, the tertiary amine preferably has a branch in the alkyl chain at the α- and/or β-carbon atom.

Examples of particularly preferred tertiary amines are tris(2-ethylhexyl)amine, tris-2-(cyclohexylethyl)amine, tris(1-methylheptyl)amine, 1,4-diazabicyclo[2.2.2]octane (TEDA), 1,5-diazabicyclo[4.3.0]non-5-ene (DBN) and 1,8-diazabicyclo[5.4.0]undec-7-ene (DBU).

Ionic liquids (IL) are liquids as are defined by Wasserscheid and Keim in Angewandte Chemie 2000, 112, pages 3926-3945. The group of ionic liquids represents a new type of solvent. As stated in the abovementioned document, ionic liquids are salts which have a nonmolecular, ionic character and melt at relatively low temperatures. They are liquid and have a relatively low viscosity even at relatively low temperatures of less than 200° C., preferably less than 150° C., particularly preferably less than 100° C. They have very good solvent capabilities for a large number of organic, inorganic and polymeric substances.

Compared to ionic salts, ionic liquids are liquid at significantly lower temperatures (in general below 200° C.) and frequently have a melting point below 0° C., occasionally as low as −96° C.

Furthermore, ionic liquids are generally noncombustible, noncorrosive and have a low viscosity and also have a non-measurable vapor pressure.

Ionic liquids are compounds which have at least one positive charge and at least one negative charge, but are overall uncharged and have a melting point below 200° C., preferably below 100° C., particularly preferably below 50° C.

The ionic liquids can also have a plurality of positive charges and correspondingly negative charges, for example from 1 to 5, preferably from 1 to 4, particularly preferably from 1 to 3, very particularly preferably 1 or 2, charges, but in particular one positive charge and one negative charge.

The charges can be located at various localized or delocalized regions within a molecule, i.e. in a betaine-like fashion, or can be distributed over a separate anion and a separate cation. Preference is given to ionic liquids which are made up of at least one cation and at least one anion.

Of course, the formation of a mixture of various ionic liquids is also conceivable in the process of the invention.

Preferred cations are ammonium or phosphonium ions or cations comprising at least one five- or six-membered heterocycle which has at least one phosphorus or nitrogen atom and, if appropriate, an oxygen or sulfur atom, also compounds which comprise at least one five- or six-membered heterocycle which has one, two or three nitrogen atoms and a sulfur atom or an oxygen atom, preferably ones having one or two nitrogen atoms.

Particularly preferred ionic liquids are ones which have a molecular weight of less than 1000 g/mol, very particularly preferably less than 500 g/mol.

Furthermore, preference is given to cations selected from among the compounds of the formulae (Ia) to (Iw),

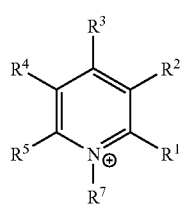

(Ia)

-continued

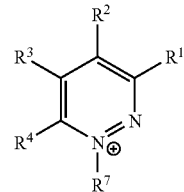

(Ib)

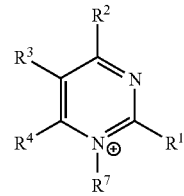

(Ic)

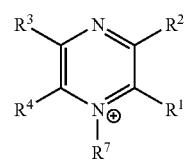

(Id)

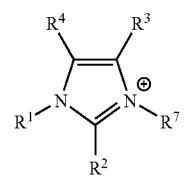

(Ie)

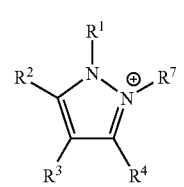

(If)

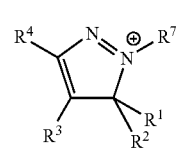

(Ig)

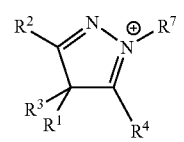

(Ih)

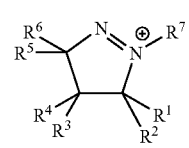

(Ii)

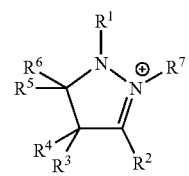

(Ij)

-continued

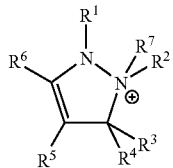
(Ik)

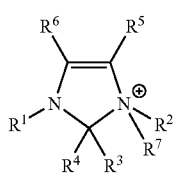
(Il)

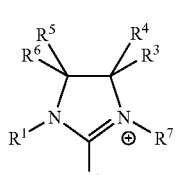
(Im)

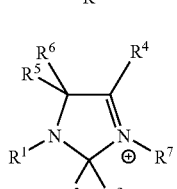
(In)

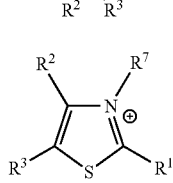
(Io)

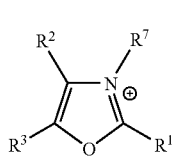
(Ip)

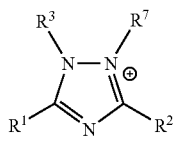
(Iq)

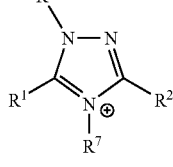
(Ir)

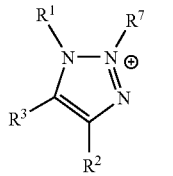
(Is)

-continued

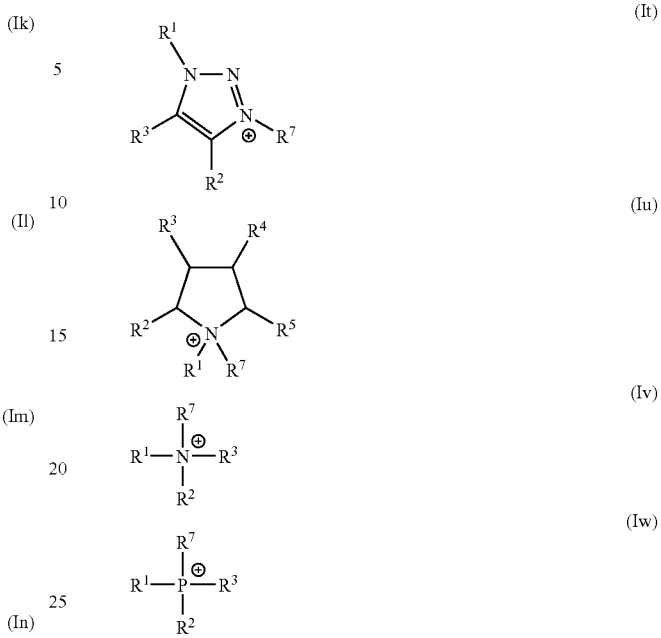

(It)

(Iu)

(Iv)

(Iw)

and oligomers and polymers comprising these structures, where $R^1$, $R^2$, $R^3$, $R^4$, $R^5$ and $R^6$ are each, independently of one another, $C_1$-$C_{18}$-alkyl, $C_2$-$C_{18}$-alkyl which may optionally be interrupted by one or more oxygen and/or sulfur atoms and/or one or more substituted or unsubstituted imino groups, $C_6$-$C_{12}$-aryl, $C_5$-$C_{12}$-cycloalkyl or a five- or six-membered, oxygen-, nitrogen- and/or sulfur-comprising heterocycle or two of them may together form an unsaturated, saturated or aromatic ring which may optionally be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles.

$R^1$, $R^2$, $R^3$, $R^4$, $R^5$ and $R^6$ can also, independently of one another, be hydrogen (H).

$R^7$ is H, with H being introduced (by protonation) by means of the hydrogen chloride (HCl) formed in the reaction according to the invention.

In these definitions, $C_1$-$C_{18}$-alkyl which may optionally be substituted by functional groups, aryl, alkyl, aryloxy, alkyloxy, halogen, heteroatoms and/or heterocycles is, for example, methyl, ethyl, n-propyl, isopropyl, n-butyl, sec-butyl, isobutyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl.

If two radicals form a ring, these radicals can together form 1,3-propylene, 1,4-butylene, 1-aza-1,3-propenylene, $1\text{-}C_1\text{-}C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not subject to any restrictions. In general, there will be no more than 5 in the radical, preferably no more than 4 and very particularly preferably not more than 3.

Furthermore, there is generally at least one carbon atom, preferably at least two carbon atoms, between any two heteroatoms.

Substituted and unsubstituted imino groups can be, for example, imino, methylimino, isopropylimino, n-butylimino or tert-butylimino.

Furthermore, functional groups are carboxy, carboxamide, hydroxy, di($C_1$-$C_4$-alkyl)amino, $C_1$-$C_4$-alkyloxycarbonyl, cyano or $C_1$-$C_4$-alkyloxy, $C_6$-$C_{12}$-aryl which may optionally be substituted by functional groups, aryl, alkyl, aryloxy, alkyloxy, halogen, heteroatoms and/or heterocycles is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl which may optionally be substituted by functional groups, aryl, alkyl, aryloxy, alkyloxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, a five- or six-membered, oxygen-, nitrogen- and/or sulfur-comprising heterocycle is, for example, furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl and $C_1$-$C_4$-alkyl is, for example, methyl, ethyl, n-propyl, isopropyl, n-butyl, sec-butyl, isobutyl or tert-butyl.

$C_1$-$C_{18}$Alkyloyl (alkylcarbonyl) can, for example, be acetyl, propionyl, n-butyloyl, sec-butyloyl, tert-butyloyl, 2-ethylhexylcarbonyl, decanoyl, dodecanoyl, chloroacetyl, trichloroacetyl or trifluoroacetyl.

$C_1$-$C_{18}$-Alkyloxycarbonyl can, for example, be methyloxycarbonyl, ethyloxycarbonyl, propyloxycarbonyl, isopropyloxycarbonyl, n-butyloxycarbonyl, sec-butyloxycarbonyl, tert-butyloxycarbonyl, hexyloxycarbonyl, 2-ethylhexyloxycarbonyl or benzyloxycarbonyl.

$C_5$-$C_{12}$-Cycloalkylcarbonyl can, for example, be cyclopentylcarbonyl, cyclohexylcarbonyl or cyclododecylcarbonyl.

$C_6$-$C_{12}$-Aryloyl (arylcarbonyl) can, for example, be benzoyl, toluyl, xyloyl, α-naphthoyl, β-naphthoyl, chlorobenzoyl, dichlorobenzoyl, trichlorobenzoyl or trimethylbenzoyl.

In the formulae Ia to Iu, preference is given to $R^1$, $R^2$, $R^3$, $R^4$, $R^5$ and $R^6$ each being, independently of one another, hydrogen, methyl, ethyl, n-butyl, 2-hydroxyethyl, 2-cyanoethyl, 2-(methoxycarbonyl)ethyl), 2-(ethoxycarbonyl)ethyl, 2-(n-butoxycarbonyl)ethyl, dimethylamino, diethylamino or chlorine.

Particularly preferred pyridinium ions (Ia) are those in which one of the radicals $R^1$ to $R^5$ is methyl, ethyl or chlorine, $R^7$ is acetyl, methyl, ethyl or n-butyl and all others are hydrogen, or $R^3$ is dimethylamino, $R^7$ is acetyl, methyl, ethyl or n-butyl and all others are hydrogen or $R^7$ is acetyl, methyl, ethyl or n-butyl and all others are hydrogen or $R^2$ is carboxy or carboxamide, $R^7$ is acetyl, methyl, ethyl or n-butyl and all others are hydrogen or $R^1$ and $R^2$ or $R^2$ and $R^3$ are together 1,4-buta-1,3-dienylene, $R^7$ is acetyl, methyl, ethyl or n-butyl and all others are hydrogen.

Particularly preferred pyridazinium ions (Ib) are those in which one of the radicals $R^1$ to $R^4$ is methyl or ethyl and all others are hydrogen.

Particularly preferred pyrimidinium ions (Ic) are those in which $R^2$ to $R^4$ are each hydrogen or methyl and $R^1$ is hydrogen, methyl or ethyl, or $R^2$ and $R^4$ are each methyl, $R^3$ is hydrogen and $R^1$ is hydrogen, methyl or ethyl.

Particularly preferred pyrazinium ions (Id) are those in which $R^1$ to $R^4$ are all methyl.

Particularly preferred imidazolium ions (Ie) are those in which, independently of one another, $R^1$ is selected from among methyl, ethyl, n-propyl, n-butyl, n-pentyl, n-octyl, n-decyl, n-dodecyl, 2-hydroxyethyl and 2-cyanoethyl, and $R^2$ to $R^4$ are each, independently of one another, hydrogen, methyl or ethyl.

Particularly preferred 1H-pyrazolium ions (If) are those in which, independently of one another, $R^1$ is selected from among hydrogen, methyl and ethyl, and $R^2$, $R^3$ and $R^4$ are selected from among hydrogen and methyl.

Particularly preferred 3H-pyrazolium ions (Ig) are those in which, independently of one another, $R^1$ is selected from among hydrogen, methyl and ethyl, and $R^2$, $R^3$ and $R^4$ are selected from among hydrogen and methyl.

Particularly preferred 4H-pyrazolium ions (Ih) are those in which, independently of one another, $R^1$ to $R^4$ are selected from among hydrogen and methyl.

Particularly preferred 1-pyrazolinium ions (Ii) are those in which, independently of one another, $R^1$ to $R^6$ are selected from among hydrogen and methyl.

Particularly preferred 2-pyrazolinium ions (Ij) are those in which, independently of one another, $R^1$ is selected from among hydrogen, methyl, ethyl and phenyl, and $R^2$ to $R^6$ are selected from among hydrogen and methyl.

Particularly preferred 3-pyrazolinium ions (Ik) are those in which, independently of one another, $R^1$ and $R^2$ are selected from among hydrogen, methyl, ethyl and phenyl, and $R^3$ to $R^6$ are selected from among hydrogen and methyl.

Particularly preferred imidazolinium ions (Il) are those in which, independently of one another, $R^1$ and $R^2$ are selected from among hydrogen, methyl, ethyl, n-butyl and phenyl, $R^3$ and $R^4$ are selected from among hydrogen, methyl and ethyl and $R^5$ and $R^6$ are selected from among hydrogen and methyl.

Particularly preferred imidazolinium ions (Im) are those in which, independently of one another, $R^1$ and $R^2$ are selected from among hydrogen, methyl and ethyl, and $R^3$ to $R^6$ are selected from among hydrogen and methyl.

Particularly preferred imidazolinium ions (In) are those in which, independently of one another, $R^1$, $R^2$ and $R^3$ are selected from among hydrogen, methyl and ethyl, and $R^4$ to $R^6$ are selected from among hydrogen and methyl.

Particularly preferred thiazolium ions (Io) or oxazolium ions (Ip) are those in which, independently of one another, $R^1$ is selected from among hydrogen, methyl, ethyl and phenyl, and $R^2$ and $R^3$ are selected from among hydrogen and methyl.

Particularly preferred 1,2,4-triazolium ions (Iq) and (Ir) are those in which, independently of one another, $R^1$ and $R^2$ are selected from among hydrogen, methyl, ethyl and phenyl, and $R^3$ is selected from among hydrogen, methyl and phenyl.

Particularly preferred 1,2,3-triazolium ions (Is) and (It) are those in which, independently of one another, $R^1$ is selected from among hydrogen, methyl and ethyl, $R^2$ and $R^3$ are selected from among hydrogen and methyl or $R^2$ and $R^3$ are together 1,4-buta-1,3-dienylene and all others are hydrogen.

Particularly preferred pyrrolidinium ions (Iu) are those in which, independently of one another, $R^1$ is selected from among acetyl, methyl, ethyl and n-butyl and $R^2$, $R^3$, $R^4$ and $R^5$ are each hydrogen.

Particularly preferred ammonium ions (Iv) are those in which, independently of one another, $R^1$, $R^2$, and $R^3$ are selected from among methyl, ethyl, n-butyl, 2-hydroxyethyl, benzyl and phenyl.

Particularly preferred phosphonium ions (Iw) are those in which, independently of one another, $R^1$, $R^2$ and $R^3$ are selected from among phenyl, phenoxy, ethoxy and n-butoxy.

Among these cations, the imidazolium, pyridinium, ammonium and phosphonium ions are preferred.

Very particularly preferred cations are 1,2-dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butylpyridinium, 1-butyl-4-methylpyridinium, 1,3-dimethylimidazolium, 1,2,3-trimethylimidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazol, 3-butyl-1-methylimidazolium, 3-butyl-1-ethylimidazolium, 3-butyl-1,2-dimethylimidazolium, 1,3-di-n-butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium, 1-decyl-3-methylimidazolium.

Especial preference is given to 1-butyl-4-methylpyridinium, 1-n-butyl-3-methylimidazolium and 1-n-butyl-3-ethylimidazolium.

In a particular embodiment, the cations are singly charged ammonium ions which are formed by protonation of the tertiary amines mentioned further above, in particular $C_{18}$-$C_{42}$-alkylamines.

Examples of such ammonium ions are tris(2-ethylhexyl)ammonium, tris(2-cyclohexyl-ethyl)ammonium and tris(1-methylheptyl)ammonium.

The anion together with the cations mentioned forms an ionic liquid. The anion is chloride which originates from the hydrogen chloride (HCl) resulting from the reaction according to the invention.

The organic nitrogen or phosphorus compound used in the process as precursor of the abovementioned ionic liquids is preferably used in an amount of greater than 100 mol %, particularly preferably greater than 150 mol %, in particular in the range from 200 to 400 mol %, in each case based on the molar amount of EDC used.

The EDC required as starting material can be prepared by known methods, for example by oxychlorination of ethylene.

In the process of the invention, preference is given to using pure EDC, e.g. EDC having a purity of ≧98% by weight, in particular ≧99% by weight.

The discontinuous or continuous reaction of EDC in a reactor, which can naturally also be divided up into two or more reactors connected in series or in parallel, can be carried out using methods based on methods known to those skilled in the art.

Preferred reactors are cascades of stirred vessels or tube reactors.

The reaction of EDC with ammonia is preferably carried out in the liquid phase.

The reaction according to the invention is preferably carried out at an absolute pressure in the range from 20 to 150 bar, preferably from 30 to 80 bar, in particular from 40 to 60 bar.

The reaction temperature is preferably in the range from 50 to 200° C., in particular from 70 to 120° C., preferably from 90 to 110° C.

EDC and ammonia are preferably used in a molar ratio in the range $EDC:NH_3=1:5-25$, in particular $EDC:NH_3=1:8-15$.

In the process of the invention, the proportion of EDA in the (total) ethylene amines formed, in particular based on the ethylene amines EDA, DETA, PIP, TETA, TEPA and PEHA formed, is preferably greater than 30% by weight, particularly preferably greater than 40% by weight, e.g. in the range from 42 to 52% by weight.

The total yield of EDA and DETA is, in particular, greater than 45%, very particularly preferably greater than 55%, in each case based on EDC used.

EDA and DETA are obtained in the reaction product from the reaction of EDC in an EDA:DETA weight ratio of, in particular, 50-90:20, e.g. 70:20. At an EDC conversion of 99%, an EDA selectivity of, for example, 50% is achieved.

Work-up of the reaction product mixture from the process of the invention:

The relatively low-boiling ethylene amines (EDA, DETA, piperazine) are preferably separated off from the liquid reaction product mixture by distillation.

The ionic liquid remaining in the bottoms is, in one embodiment of the process, admixed with sodium hydroxide so that the organic nitrogen or phosphorus compound used in the process, e.g. the tertiary amine or the imidazole, is set free and, after phase separation, can be recirculated to the synthesis or the ethylene amine distillation.

This can be seen in scheme 1 shown by way of example in the appendix.

In an alternative work-up variant, the organic nitrogen or phosphorus compound which reacts with hydrogen chloride to form an ionic liquid (IL) is selected so that the ionic liquid formed forms a second phase with the ethylene amine mix. In this case, the ethylene amines are separated from the ionic liquid by phase separation and the ionic liquid is treated with sodium hydroxide to set the organic nitrogen or phosphorus compound used in the process, e.g. the tertiary amine or the imidazol, free.

This can be seen in scheme 2 shown by way of example in the appendix.

A further alternative way of recovering and recirculating the organic nitrogen or phosphorus compound used in the process, e.g. the tertiary amine or the imidazole, is thermal dissociation of the hydrochloride into HCl and nitrogen or phosphorus compound, e.g. tertiary amine or imidazole, and separation of the two components in a reactive distillation. In this case, the solvents have to have a high thermal stability and acid resistance so that the solvent is not destroyed in the thermal dissociation of the hydrochloride.

An advantage of this variant is, in particular, that no sodium hydroxide has to be used This can be seen in scheme 3 and the variant thereof in scheme 4 shown by way of example in the appendix.

In the work-up variants described, the organic nitrogen or phosphorus compound which is used in the process and recovered, e.g. the tertiary amine or the imidazole, can be distilled to avoid accumulation of high boilers, e.g. high-boiling ethylene amines, before recirculation.

The work-up of the ethylene amine product streams obtained in the process of the invention, which comprise, in particular, the particularly desired EDA and also DETA, triethylenetetramine (TETA), tetraethylenepentamine (TEPA) and/or pentaethylenehexamine (PEHA), can be carried out by distillation methods known to those skilled in the art, e.g. by multistage distillation.

The distillation columns required for recovery of the individual products, especially the particularly desired EDA, in pure form by distillation can be designed by those skilled in the art using methods with which they would be familiar (e.g. a number of theoretical plates, reflux ratio, etc.).

Ammonia obtained in the fractionation of the reaction product mixture resulting from the reaction is preferably recirculated to the reaction.

The invention claimed is:

1. A process comprising: (i) providing a reactant comprising 1,2-dichloroethane; and (ii) reacting the reactant with ammonia to form a reaction product comprising one or more ethylene amines and hydrogen chloride, wherein the reaction is carried out in the presence of an organic, nitrogen- or phosphorus-containing compound which reacts with the hydrogen chloride to form an ionic liquid, wherein the organic, nitrogen- or phosphorus-containing compound comprises one or more selected from the group consisting of tertiary amines, N-heterocycles, tertiary phosphanes, and mixtures thereof.

2. The process according to claim 1, wherein the one or more ethylene amines comprises a compound selected from the group consisting of ethylenediamine (EDA), diethylenetriamine (DETA), piperazine (PIP), triethylenetetramine (TETA), tetraethylenepentamine (TEPA), pentaethylenehexamine (PEHA), and mixtures thereof.

3. The process according to claim 1, wherein the ammonia reacted with the reactant is present as a liquid or an aqueous solution.

4. The process according to claim 1, wherein the one or more ethylene amines comprises ethylenediamine (EDA) in an amount greater than 30% by weight based on the one or more ethylene amines.

5. The process according to claim 1, wherein the organic, nitrogen- or phosphorus-containing compound comprises one or more selected from the group consisting of tertiary amines of the formula $R^1R^2R^3N$, tertiary phosphanes of the formula $R^1R^2R^3P$, and mixtures thereof, wherein $R^1$, $R^2$ and $R^3$ each independently represent a $C_{1-18}$-alkyl, $C_{6-12}$-aryl or $C_{5-12}$-cycloalkyl group.

6. The process according to claim 1, wherein the organic, nitrogen- or phosphorus-containing compound comprises a tertiary amine having a boiling point at atmospheric pressure of greater than 100° C. and the corresponding acid obtained by protonation of the tertiary amine has a $pK_a$ at 25° C. or greater than 8.5.

7. The process according to claim 1, wherein the organic, nitrogen- or phosphorus-containing compound comprises a tertiary $C_{18-14}$-alkylamine.

8. The process according to claim 1, wherein the organic, nitrogen- or phosphorus-containing compound comprises a tertiary alkyl amine having a branch in the alkyl chain at the α-carbon atom, the β-carbon atom or both.

9. The process according to claim 1, wherein the organic, nitrogen- or phosphorus-containing compound comprises an aliphatic or aromatic N-heterocycle having 2 to 5 ring carbons.

10. The process according to claim 1, wherein reacting the reactant with the ammonia is carried out at a temperature of 50 to 200° C.

11. The process according to claim 1, wherein reacting the reactant with the ammonia is carried out at an absolute pressure of 20 to 150 bar.

12. The process according to claim 1, wherein the reactant and the ammonia are reacted at a molar ratio of 1,2-dichloroethane:ammonia of 1:5 to 1:25.

13. The process according to claim 1, wherein reacting the reactant with the ammonia is carried out in the liquid phase.

14. The process according to claim 1, wherein reacting the reactant with the ammonia is carried out in a cascade of stirred vessels or a tube reactor.

15. The process according to claim 1, wherein the one or more ethylene amines are separated from the reaction product by distillation.

16. The process according to claim 1, wherein the one or more ethylene amines are separated from the reaction product by phase separation.

17. The process according to claim 1, further comprising treating the ionic liquid to free the organic, nitrogen- or phosphorus-containing compound; and recycling the freed organic, nitrogen- or phosphorus-containing compound to the reaction of the reactant with the ammonia; wherein treating the ionic liquid comprises thermal treatment, contacting the ionic liquid with an alkali, or both.

18. The process according to claim 1, further comprising separating unreacted ammonia from the reaction product and recycling the unreacted ammonia to the reaction of the reactant with the ammonia.

19. A process comprising: (i) providing a reactant comprising 1,2-dichloroethane; and (ii) reacting the reactant with liquid or aqueous ammonia to form a reaction product comprising one or more ethylene amines and hydrogen chloride; wherein the reaction is carried out at a temperature of 50 to 200° C. and an absolute pressure of 20 to 150 bar, in the presence of an organic, nitrogen- or phosphorus-containing compound which reacts with the hydrogen chloride to form an ionic liquid, wherein the organic, nitrogen- or phosphorus-containing compound comprises one or more selected from the group consisting of tertiary amines, N-heterocycles, tertiary phosphanes, and mixtures thereof wherein the reactant and the ammonia are reacted at a molar ratio of 1,2-dichloroethane:ammonia of 1:5 to 1:25; and wherein the one or more ethylene amines comprises ethylenediamine (EDA) in an amount greater than 30% by weight based on the one or more ethylene amines.

* * * * *